United States Patent [19]

Kutner

[11] 4,204,328
[45] May 27, 1980

[54] VARIABLE DIAMETER ASPIRATING TIP

[76] Inventor: Barry S. Kutner, 8 Crossland Rd., Norwalk, Conn. 06851

[21] Appl. No.: 851,109

[22] Filed: Nov. 14, 1977

[51] Int. Cl.² .............................................. A61C 17/04
[52] U.S. Cl. ..................................... 433/29; 128/276; 239/546; 15/418; 433/96
[58] Field of Search .......................... 32/33; 128/276; 239/546, 602; 15/418; 251/155

[56] References Cited

U.S. PATENT DOCUMENTS

| | | | |
|---|---|---|---|
| 1,865,012 | 6/1932 | Jackson | 239/602 |
| 2,255,657 | 9/1941 | Freedman | 32/33 |
| 2,608,053 | 8/1952 | Davidson | 239/546 |
| 3,208,145 | 9/1965 | Turner | 32/33 |
| 3,254,869 | 6/1966 | Easey | 239/546 |
| 3,589,363 | 6/1971 | Banko | 128/276 |
| 3,645,497 | 2/1972 | Nyboer | 32/33 |
| 3,913,231 | 10/1975 | Orsing | 32/33 |
| 3,958,573 | 5/1976 | Wiley | 128/276 |

*Primary Examiner*—Louis G. Mancene
*Assistant Examiner*—John J. Wilson
*Attorney, Agent, or Firm*—Arthur T. Fattibene

[57] ABSTRACT

A variable diameter aspirating tip adapted to be connected at the end of a suction hose which comprises a conduit section having connected to one end a nozzle formed of a flexible material which defines an orifice capable of expanding between a minimal diameter and a maximal diameter. An expander, slidably disposed within the flexible nozzle, is connected to an actuator. The expander is normally proportioned so as to have a diameter greater than the minimal diameter of the orifice. By effecting relative displacement between the expander and the nozzle, the size or diameter of this orifice is varied accordingly.

16 Claims, 15 Drawing Figures

U.S. Patent  May 27, 1980  Sheet 1 of 3  4,204,328
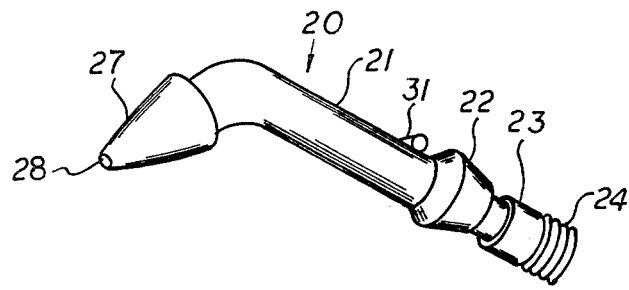
FIG. 1
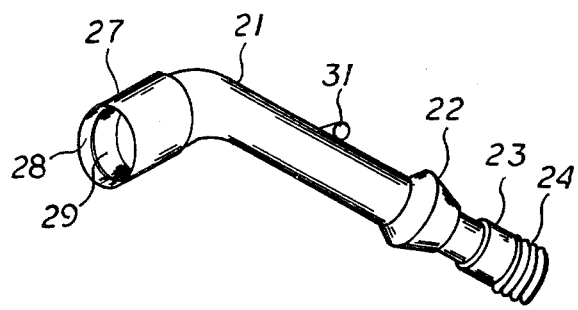
FIG. 2
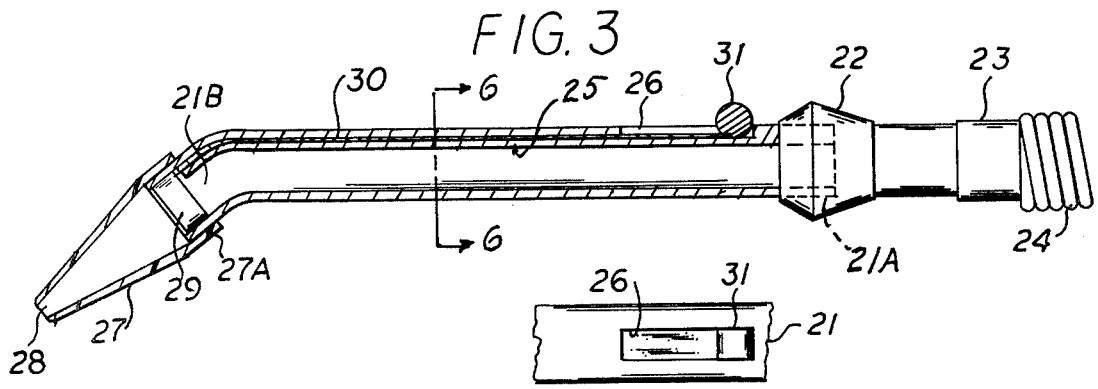
FIG. 3
FIG. 5
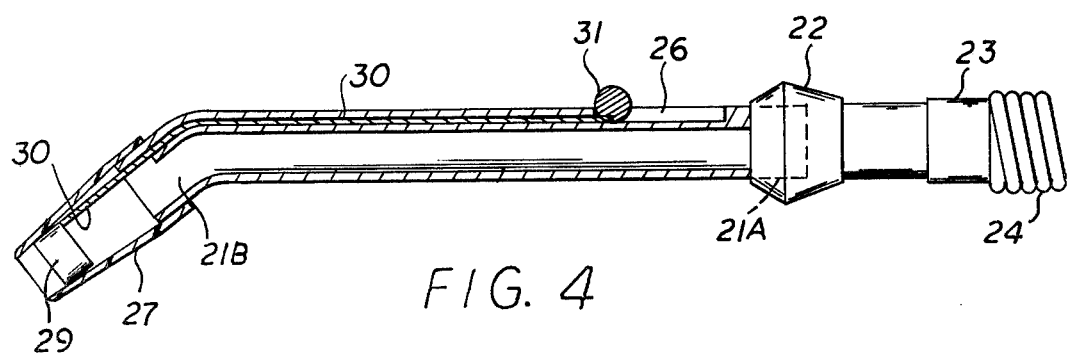
FIG. 4

VARIABLE DIAMETER ASPIRATING TIP

Problem and Prior Art

In the performance of various surgical procedures, e.g., by a dentist or physician, it is essential to keep the operating area clear and dry. This is effected with the aid of high volume suction equipment which enables the surgeon or his assistant to remove blood, fluids, debris, water, saliva, etc., from the operating field. Heretofore, such suction equipment included an aspirating nozzle having a fixed predetermined orifice opening which was placed into the operating field to effect the removal of blood or debris. As the orifice opening of the known aspirating tips are fixed or have predetermined size of opening, such tips would quickly and frequently be subjected to blockages. When such blockages would occur, the surgeon or assistant handling the aspirating device would have to cease his function in order to clear the blockage. This clearing of the blockage was generally effected by ramming the orifice clear with a wire or other suitable ramming or clearing device, or by the suction of water through the blocked nozzle to wash this blockage away; or if the tip could not be readily unblocked, to replace the blocked tip with another tip. As a result, whenever, such blockage occurred, the continued accumulation of blood and/or fluids during the operating procedure would seriously interfere with the operation as the surgeon or assistant was clearing the blockage.

While the known aspirating tips have been made in various sizes and shapes, they included a fixed orifice opening which was easily blocked, and/or included a valving member to control the degree of suction directed to an operating area. Such prior known operating tips are evidenced by U.S. Letters Pat. Nos. 3,232,578; 3,645,497; and 3,913,231. Such aspirating nozzle could not be varied in size of orifice opening. Heretofore, any variety in orifice sizing had to be effected by interchanging one size aspirator tips for that of another. This required one to have a number of aspirator tips varying in sizes over a given range of sizes.

Objects

An object of the invention is to provide a single aspirating tip in which the orifice opening can be readily varied between a minimal and maximal diameter opening to cover a predetermined range of orifice openings.

Another object is to provide an aspirating tip which can be readily unblocked, in the event of blockage, without interrupting the operating procedure and/or removing the aspiration from the operating area.

Another object is to provide an improved variable aspirating tip which can be readily operated with one hand thereby leaving the operator's other hand free to perform other functions.

Another object is to provide an aspirating tip having a variable orifice opening in which a blockage thereof can be readily cleared by simply temporarily enlarging the orifice opening.

Another object is to provide a single aspirating tip having variable orifice opening and which tip is provided with lumination.

BRIEF SUMMARY OF THE INVENTION

The foregoing objects and other features and advantages of this invention are attained by an aspirating tip which can be readily attached to the end of a suction hose. The aspirating tip comprises a conduit section having an outlet end portion which can be detachably connected to an end adapter of a suitable seuction hose. A nozzle formed of a resilient or flexible material is connected at the other end of the conduit. The nozzle is formed of a generally concical shape having its small end defining an orifice opening. An expander in the form of a ring or sleeve is slidably disposed within the nozzle. Connected to the ring or sleeve is an activator to retract and protract the ring or sleeve relative to the nozzle. The arrangement is such that the protraction of the ring or sleeve relative to the nozzle will cause the orifice to expand. Retraction of the ring or sleeve causes the orifice opening to restrict. In operation, a blocked orifice opening can be readily unclogged by effecting a temporary enlargement of the orifice. Also the degree of vacuum or negative pressure can be controlled by regulating the size of the orifice. In another embodiment, a source of illumination is provided to illuminate the operating area.

Features

A feature of this invention resides in the provision of an aspirating tip or nozzle which is formed of a readily expandable material which has slidably disposed therein an expander to control the size of the orifice.

Another feature resides in the provision of an aspiration nozzle having an expander therein which is remotely activated to control the diameter or size of the orifice opening.

Another feature resides in the provision of an aspirating tip which is relatively simple in construction, relatively inexpensive to manufacture, and which is positive in operation.

Another feature of the invention resides in the provision of an improved aspirating tip having a variable or adjustable orifice which can be readily adapted for use with existing vacuum or negative pressure suction apparatus; and which may include a source of illumination.

Other features and advantages will become more readily apparent when considered in view of the drawings and specification in which:

FIG. 1 is a perspective view of an aspirating tip embodying the present invention illustrating the minimal orifice diameter.

FIG. 2 is a view similar to FIG. 1 but illustrating the maximal opening of the orifice of the aspirating tip.

FIG. 3 is a cross section view of the aspirating tip of FIG. 1.

FIG. 4 is a cross sectioned view of the aspirating tip as shown in FIG. 2.

FIG. 5 is a fragmentary top plan view of FIG. 3.

DETAILED DESCRIPTION

Figure 6:
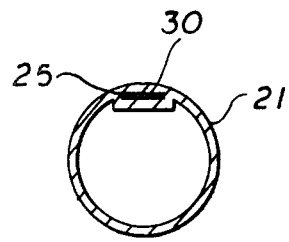
FIG. 6 is a section view taken along line 6—6 on FIG. 3.

Referring to the drawing there is shown in FIGS. 1 to 8 inclusive, an improved aspirating tip embodying the present invention. The aspirating tip to be described is particularly applicable for use by dentist and physicians during a surgical procedure. During such procedure, it is imperative to effect the removal of blood, fluids, and debris from the operating area so as to keep the area dry and clear. This is effected with the aid of high volume suction equipment.

The aspirating tip 20 embodying the present invention for use with such suction equipment comprises a tubular section or conduit 21 which is adapted to be detachably connected at its outlet end 21A to an adapter or coupling 22 which is usually connected to the end 23 of a suction hose 24. It will be understood that the hose 24 is suitable connected to a source of negative pressure or vacuum (not shown).

In this illustrated embodiment the tube or conduit 21 is of generally uniform cross-section which may be angularly bent adjacent the inlet end 21B. As best seen in FIG. 6, the tube or conduit has a channelway 25 formed therein which extends substantially the length of conduit 21. Adjacent the outlet end 21A of conduit 21 there is formed a slot 26. The arrangement is such that the channelway 25 communicates or terminates with slot 26.

Connected to the inlet end 21B of conduit 21 is nozzle 27. According to this invention the nozzle 27 is formed of a suitable expandible or flexible material which can readily stretched or expanded or will be hereinafter described. The nozzle can then be fabricated of rubber, plastic or even metal as will be hereinafter described.

As shown the nozzle 27 is generally frustro conical in shape having its normally smaller end defining the orifice or opening 28. The larger or outlet end 27A of the nozzle is suitably connected to the end 21B of conduit 21.

An expander in the form of a ring 29 is slidably disposed with nozzle 27. As shown the expander or ring is provided with a diameter substantially equal to the diameter of the conduit 21 or internal diameter of the outlet end 27A of the nozzle. The expander or ring 29 is connected to an actuating member in the form of a rail or slide 30. It will be understood that the rail or slide 30 is sufficiently rigid and flexible so as to be rendered readily displaceable within the channelway 25 so as to effect the protraction and retraction of the ring 29 within the nozzle 27.

An operating knob 31 is connected to the remote end of rail or slide 30 which projects through slot 26. It will then be apparent that when the knob 31 is displaced to the left as view in FIG. 1 that the ring 29 connected thereto will be protracted relative to conduit 21 to a position indicated in FIG. 4. Because the diameter of the ring is greater than the normal orifice opening 28 an view in FIGS. 1 & 3, the orifice or opening 28 is expanded in the protracted position of ring 29; as shown in FIGS. 2 & 4. It will therefore be apparent that the relative position of the ring between its limits of travel will vary the size of the orifice or opening 28 accordingly. In the illustrated embodiment, the orifice open can be expanded from a ⅛ in. I.D. opening to a ⅜ in. I.D. opening. However, it will be understood that the range of expansion can vary depending upon a given application. The foregoing defined range is deemed to be satisfactory for most dental or surgical procedures.

It will be understood that the conduit portion 21 may be formed of either metal or plastic which can be readily fabricated so that it can be sterilized and reused or in the alternative can be fabricated of relative inexpensive materials so that the tip can be made expendible after each use.

Figure 8:
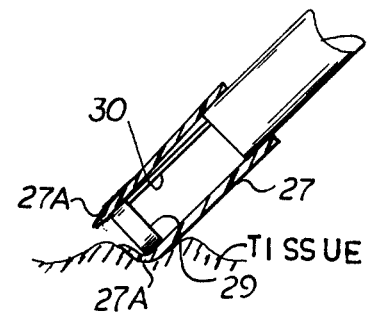
FIG. 8 is a detail sectioned view of the aspirating tip illustrating a useful feature thereof.
Figure 7:
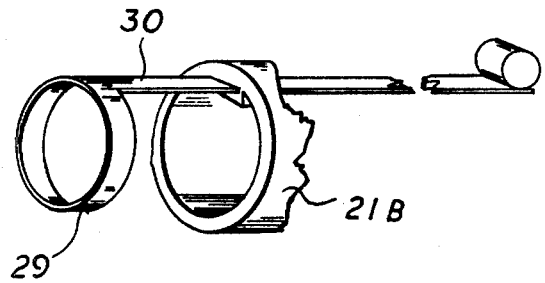
FIG. 7 is a fragmentary perspective view of a detail of construction.

As shown in FIG. 8, the nozzle is proportioned so as to be slightly longer than the protracted distance of ring 29. Because of this, the projecting portion 27A of the nozzle defines a flexible rim or lip so that any tissue adjacent the tip end of the nozzle is protected from damage or abuse. Also the soft lip or rim 27A defined will function to deflect soft tissue, and thus lessen the chance of soft tissue being drawn into the orifice 28 to block it.

Figure 9:
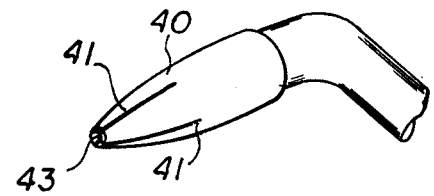
FIG. 9 is a perspective view of a modified embodiment.
Figure 10:
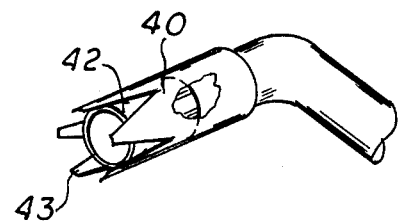
FIG. 10 is a view similar to FIG. 9, but illustrating the aspirating tip in the expanded orifice position.

FIGS. 9 & 10 illustrates a slightly modified embodiment. In this form of the invention, the nozzle 40 is provided with a plurality of circumferentially spaced slits 41 which in its normal position as shown in FIG. 9 defines a conical shaped nozzle. The expander in this form of the invention comprises a ring or sleeve 42 which is slidably disposed in a manner as hereinbefore described with respect to FIGS. 1 to 8. Thus as seen in FIG. 10, the orifice or opening 43 is expanded as the sleeve or ring 42 is protracted. By forming the expander as in sleeve 42, it will be noted that the tubular sleeve 42 will function to seal the side opening as the slits 41 open upon the expanding of nozzle 40. Forming the expander 42 as a ring will permit the slits 41 to become side openings to permit some fluid to be rushed in from the side opening as well as from the front. In certain procedures this may be desirable.

With the construction shown in FIGS. 9 & 10, the nozzle can be fabricated of a spring metal as well as rubber or flexible plastics. In all other respects the construction and operation of the aspirator tip of FIGS. 9 & 10 is similar to that hereinbefore described with respect to FIGS. 1 to 8.

In operation the aspirator tip herein described can be readily used in a manner similar to known aspirators. However, in the event that a blockage should occur, the operator need only protract the ring or sleeve to enlarge the orifice or opening 28, whereby the material causing the blockage is quickly and easily sucked into the large bore of the conduit 21. Once cleared, the operator can immediately return to the desired orifice setting thereby effectively causing the fluids and debris to be removed from the operating area without interruption.

The structure of the instant described aspirator can be readily formed of material which can make them disposable or sterilizable for repeated use. The nozzle when formed of plastic or rubber would be non-conductive permitting its use in electrosurgical and electrocautery procedures.

While the present invention has been described for use in surgical procedures, it will be understood that the nozzle described may have application in industry to effect the removal of liquids, gases, or solids. The foregoing described nozzle provides for a simple, expedient and positive manner by which the nozzle can be readily cleared of blockage, and a simple system for varying the size of the orifice opening in situ.

Figure 11:
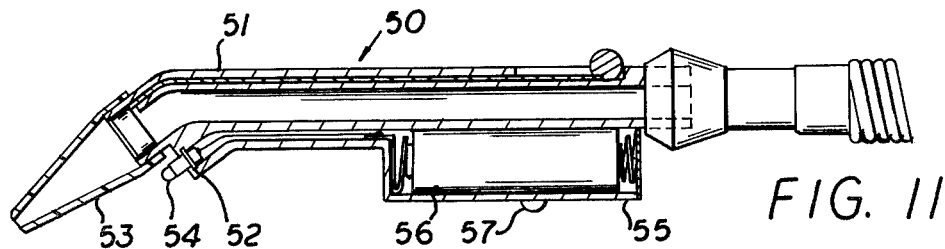
FIG. 11 is a sectional side view of a modified embodiment to include a light source for illumination.

FIG. 11 illustrates another embodiment of the invention. In this form of the invention, the aspirator 50 is similar to that described with respect to FIGS. 1 to 8 or 9 and 10, except that in this form, a means is provided for illumination. It will be understood that in certain operating procedures, occuring deep within a body cavity, illumination is frequently necessary. For such a procedure, the aspirating tip 50 is provided with a contained means of illumination. As shown, the conduit portion 51 is provided with a bulb seat 52 adjacent the nozzle tip 53 for receiving a light bulb 54. Connected or adjacent to the conduit portion 51 is a housing 55 for containing a battery 56 for energizing the bulb 54. It will be understood that this bulb is connected in circuit with the battery whereby the bulb 54 can be energized at will by actuation of a switch 57.

Figure 12:
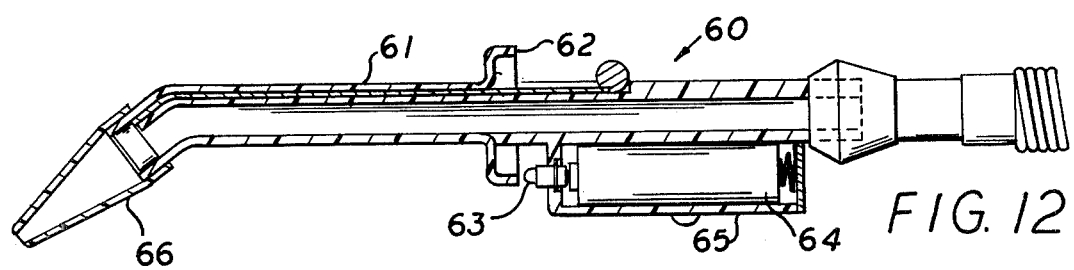
FIG. 12 is a sectional side view of another illuminated embodiment of the invention.

FIG. 12 illustrates another illuminated embodiment. In this form of the invention the aspirator 60 is provided with a conduit section or portion 61 which is formed of Lucite type of material which is capable of directing light therethrough.

In this form of the invention the conduit portion 61 is provided with a flange 62 which is disposed opposite to a bulb 63.

The bulb 63 is connected in circuit to a power supply, e.g., a battery 64 mounted in a housing 65 connected to the conduit 61. The light circuit as described with respect to FIG. 11 is provided with a suitable switch to make and break the circuit to the light bulb.

With the structure described, it will be noted that the nozzle or tip 66 is formed of a light transmitting flexible material so that the light directed through the Lucite body or conduit will project through the nozzle or tip 66 to light up an operating area when in use. In all other respects, the structure and function of the aspirator 60 is similar to that hereinabove described.

Figure 14:
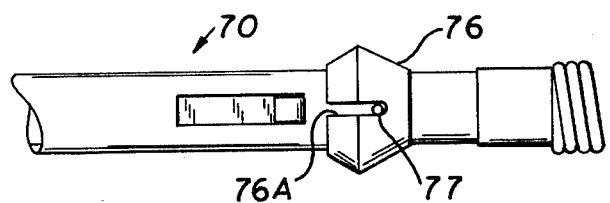
FIG. 14 is a fragmentary top plan view of FIG. 13.
Figure 13:
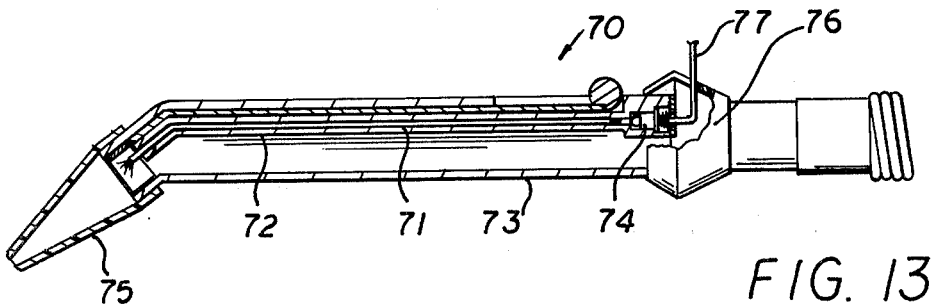
FIG. 13 is a sectional side view of still another illuminated embodiment of the invention.

FIGS. 13 and 14 illustrate another illuminated embodiment. In this form of the invention the aspirator 70 is provided with a bundle of fiber optic elements 71 disposed in a channel 72 disposed either internally or externally of the conduit portion 73. In the illustrated embodiment, the channel 72 containing the fiber optics 71 is disposed internally of the conduit 73. A light bulb 74 is located adjacent one end; i.e., the inner end of the fiber optic element 71. The other end of the fiber optic bundle is disposed adjacent the nozzle tip 75. It will be understood that the bulb is connected to a suitable power supply, e.g., a battery or line current not shown. Thus whenever the light bulb 74 is energized, the light is transmitted through the fiber optic elements or bundle 71 to illuminate the area in the vicinity of the nozzle 75. In all other respects the operation and function of the aspirator 70 is similar as hereinbefore described.

As shown in FIGS. 13 and 14, the coupling 76 is provided with a notch 76A to accommodate the leads or conductors 77 for connecting the light source or bulb 74 to a power supply.

Figure 15:
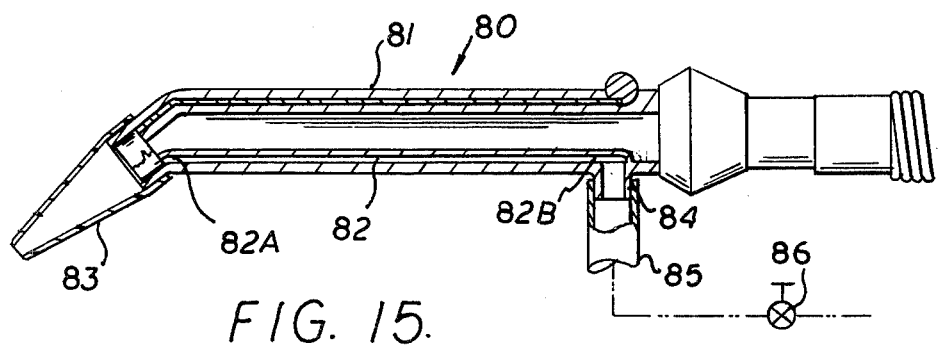
FIG. 15 is a sectional view of another modified embodiment of the invention.

FIG. 15 illustrates a further embodiment of the invention. In this form of the invention, the aspirator 80 is similar in all respects to the respective aspirators hereinbefore described with respect to FIGS. 1 to 13, but differs therefrom by the inclusion of a means to provide for irrigating the operating area. In certain operating procedures, irrigation and flushing of the surgical area is frequently necessary. Where such irrigation is necessary or desirable, the aspirator conduit portion 81 is provided with a narrow channel or tube 82 to define a passageway which can be readily connected to an external water supply, not shown. As shown, the channel or tube 82 extends along the interior of the aspirator conduit 82, the outlet 82A being disposed adjacent the aspirating tip 83. It will be understood that the channel 82 could be disposed externally of the conduit 81.

The inlet end 82B of the channel or tube 82 connects to a nipple 84 to which a flexible water supply pipe 85 can be readily detachably connected. Therefore, whenever it is desirable to utilize the aspirator 80 of FIG. 15 with irrigation, one need only to attach the water supply pipe or tube 85 to nipple 84. It will be understood that a suitable valve means may be disposed in the irrigation system described to control the flow of water through the described irrigation system. In the illustrated embodiment, the valve 86 is located in the water line 85. It will be understood that other irrigating solutions may be used other than water, e.g., a normal saline solution and such. In all other respects the construction and operation is similar to that hereinbefore described.

While the instant invention has been described with respect to several embodiments thereof, it will be readily appreciated and understood that variations and modification may be made without departing from the scope or spirit of this invention.

What is claimed is:

1. A variable diameter aspirator tip adapted to be connected to the end of a suction hose connected to a source of negative pressure comprising,
   a conduit having an inlet end and an outlet end,
   said outlet end being adapted to connected to a suction hose,
   a flexible nozzle tip connected to said inlet end of said conduit,
   said nozzle tip having orifice opening capable of expanding between a minimum and maximum diameter,
   a sliding means slidably disposed with said nozzle tip for expanding said orifice opening between said minimum and maximum diameter,
   and an actuator connected to said sliding means for shifting said sliding means relative to said nozzle for expanding said orifice opening accordingly,
   wherein said sliding means comprises a ring slidably disposed within said nozzle, said ring having a diameter substantially equal to the maximum diameter orifice opening:
   and said actuator being connected to said ring for slidably displacing said ring relative to said nozzle whereby the displacement of said ring relative to said flexible nozzle causes said orifice to expand between a minimum and maximum diameter.

2. A variable diameter aspirator tip as defined in claim 1 and including means for illuminating an area in the vicinity of said orifice opening.

3. A variable diameter aspirator tip as defined in claim 2 wherein said illuminating means comprises a light source connected to said conduit adjacent the inlet end thereof, and
   a power source connected in circuit with said light source.

4. A variable diameter aspirator tip as defined in claim 3 wherein said power source includes a battery,
   and a housing connected to said conduit adapted to contain said battery whereby said illuminating means and conduit defines a wholly self-contained unit.

5. A variable diameter aspirator tip as defined in claim 3 wherein said conduit is formed of a light transmitting material, and said light source is connected opposite one end of said light transmitting conduit.

6. A variable diameter aspirator tip as defined in claim 2 wherein said illuminating means comprises a fiber optic bundle extending longitudinally of said conduit, and
- a light source disposed adjacent one end of said fiber optic bundle,
- and said bundle having its other end disposed adjacent said nozzle whereby the light is transmitted through said fiber optic bundle from said light source to said nozzle.

7. A variable diameter aspirating tip as defined in claim 1 and including means for directing an irrigating fluid to an operating area in the vicinity of the nozzle tip.

8. A variable diameter aspirating tip as defined in claim 7 wherein said irrigating means includes:
- a channelway extending along said conduit,
- said channelway having an outlet disposed adjacent said nozzle tip, and an inlet,
- a nipple connected in communication with said inlet,
- and a supply tube connected to said nipple for directing an irrigating fluid to said channelway,
- and a valve means for controlling the flow of irrigating fluid through said channelway.

9. A variable diameter aspirator tip adapted to be detachably connected to the end of a suction hose connected at a source of negative pressure comprising:
- a conduit having an inlet end and an outlet end,
- said outlet end of said conduit being adapted to be detachably connected to the end of a suction hose,
- said conduit having a longitudinal slot formed therein adjacent the outlet end thereof,
- a channelway extending longitudinally of said conduit from said inlet end to said slot whereby said channel is disposed in communication with said slot,
- a rail slidably mounted in said channel, said rail extending substantially the length of said channelway,
- an expander connected to an end of said rail,
- said expander being normally disposed immediately adjacent the inlet end of said conduit,
- said rail having its other end disposed opposite said slot,
- an operating knob connected to said other end of said rail,
- said knob extending through said slot to facilitate the actuation of said rail and connected expander,
- a nozzle connected to the inlet end of said conduit whereby said expander is disposed within said nozzle,
- said nozzle being formed of a flexible material, and said nozzle having an orifice opening capable of expanding between a minimum and maximum diameter, whereby said orifice opening is normally of minimal diameter in the retracted position of said expander relative to said conduit and is of maximal diameter in the protracted position of said expander.

10. A variable diameter aspirator tip as defined in claim 9 wherein the orifice opening projects beyond the end of said expander in the protracted position thereof.

11. A variable diameter aspirator tip as defined in claim 9 wherein said nozzle is frusto conical in shape having its smaller end defining said orifice opening, and having its larger end connected to the inlet end of said conduit,
- and said expander having a diameter equal to the diameter of said conduit and which defines the maximal diameter of said orifice opening in the protracted position thereof.

12. A variable diameter aspirator tip as defined in claim 9 wherein said expander comprises a ring.

13. A variable diameter aspirator tip as defined in claim 9 wherein said nozzle includes a plurality of longituding extending slits formed therein to provide for an expandible orifice opening, and
- said expander includes a sleeve whereby the retraction and protraction of said sleeve within said nozzle control the size of the orifice opening accordingly.

14. A variable diameter aspirator tip adapted to be connected to the end of a suction hose connected to a source of negative pressure comprising,
- a conduit having an inlet end and an outlet end,
- said outlet end being adapted to connect to a suction hose,
- a flexible nozzle tip connected to said inlet end of said conduit,
- said nozzle tip having an orifice opening capable of expanding between a minimum and maximum diameter,
- a sliding means slidably disposed with said nozzle tip for expanding said orifice opening between said minimum and maximum diameter,
- and an actuator connected to said sliding means for shifting said sliding means relative to said nozzle for expanding said orifice opening accordingly,
- wherein said nozzle tip is generally frusto conical in shape having its smaller end defining
- an orifice opening, and having its larger end connected to said inlet end of said conduit,
- said nozzle having longitudinally extending slit formed therein to facilitate the expansion of said orifice opening between the minimum and maximum diameter,
- and said sliding means including a tubular sleeve of generally uniform diameter,
- said sleeve being slidably disposed within said nozzle for movement between a retracted and protracted position so that in the protracted position, said sleeve causes said orifice opening to expand.

15. A variable diameter aspirator tip as defined in claim 14 wherein said actuating means comprises a flexible rail,
- said rail having an end connected to said sleeve, and having its other end extending into said conduit,
- said conduit having a slot formed therein remote from said nozzle,
- and a handle means connected to said other end of said rail, said handle means extending through said slot for facilitating the shifting of said rail relative to said conduit.

16. An variable diameter aspirating tip as defined in claim 15 wherein said conduit includes a channel formed along the length thereof for accommodating said rail in sliding relationship within said channel.

* * * * *